US010456038B2

(12) United States Patent
Lamego et al.

(10) Patent No.: US 10,456,038 B2
(45) Date of Patent: Oct. 29, 2019

(54) CLOUD-BASED PHYSIOLOGICAL MONITORING SYSTEM

(71) Applicant: Cercacor Laboratories, Inc., Irvine, CA (US)

(72) Inventors: Marcelo M. Lamego, Cupertino, CA (US); Abraham Mazda Kiani, San Juan Capistrano, CA (US); Don Sanders, Irvine, CA (US); Jeroen Poeze, Rancho Santa Margarita, CA (US); Massi Joe E. Kiani, Laguna Niguel, CA (US); Anthony Amir Davia, Laguna Beach, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 507 days.

(21) Appl. No.: 14/203,243

(22) Filed: Mar. 10, 2014

(65) Prior Publication Data

US 2014/0275835 A1 Sep. 18, 2014

Related U.S. Application Data

(60) Provisional application No. 61/801,464, filed on Mar. 15, 2013, provisional application No. 61/841,346, (Continued)

(51) Int. Cl.
*A61B 5/00* (2006.01)
*A61B 5/1455* (2006.01)
*G16H 50/30* (2018.01)

(52) U.S. Cl.
CPC ........ *A61B 5/0022* (2013.01); *A61B 5/14551* (2013.01); *G16H 50/30* (2018.01); *A61B 5/7235* (2013.01)

(58) Field of Classification Search
CPC . A61B 5/0022; A61B 5/14551; A61B 5/7235; A61B 5/0004; A61B 5/0205; A61B 5/7275; G06F 19/3431; G06F 19/3418
(Continued)

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

EP 2 278 508 1/2011
WO WO 2012/099534 7/2012

OTHER PUBLICATIONS

Xiaomao Fan et al., "HCloud: A novel application-oriented cloud platform for preventive healthcare," Cloud Computing Technology and Science (CLOUDCOM), Dec. 3, 2012, pp. 705-710.
(Continued)

*Primary Examiner* — Nathan J Jenness
(74) *Attorney, Agent, or Firm* — Knobbe Martens Olson & Bear LLP

(57) ABSTRACT

A cloud-based physiological monitoring system has a sensor in communications with a living being so as to generate a data stream generally responsive to a physiological condition of the living being. A monitor receives the data stream from the sensor and transmits the data stream to a cloud server. The cloud server processes the data stream so as to derive physiological parameters having values responsive to the physiological condition. The cloud server derives a medical index based upon a combination of the physiological parameters. The cloud server communicates the medical index to the monitor, which displays the medical index.

9 Claims, 11 Drawing Sheets

Related U.S. Application Data filed on Jun. 30, 2013, provisional application No. 61/885,491, filed on Oct. 1, 2013, provisional application No. 61/922,861, filed on Jan. 1, 2014.

(58) Field of Classification Search
USPC ........................................................ 600/301
See application file for complete search history.

(56) References Cited

U.S. PATENT DOCUMENTS

| | | | |
|---|---|---|---|
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,565,976 A * | 10/1996 | Fieggen | G01N 21/7703 |
| | | | 250/227.16 |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,648,820 B1 * | 11/2003 | Sarel | A61B 5/0002 |
| | | | 128/903 |
| 6,650,917 B2 | 11/2003 | Diab et al. | |
| 6,654,624 B2 | 11/2003 | Diab et al. | |
| 6,658,276 B2 | 12/2003 | Kiani et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |

(56) References Cited

U.S. PATENT DOCUMENTS

| | | |
|---|---|---|
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |

(56) References Cited

U.S. PATENT DOCUMENTS

| | | |
|---|---|---|
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 2004/0034289 A1* | 2/2004 | Teller ............... A61B 5/02055 600/300 |
| 2005/0228298 A1* | 10/2005 | Banet ................ A61B 5/0205 600/485 |
| 2009/0149724 A1* | 6/2009 | Mark ................ A61B 5/0205 600/301 |
| 2010/0099964 A1* | 4/2010 | O'Reilly ........... A61B 5/14546 600/323 |
| 2010/0217099 A1* | 8/2010 | LeBoeuf .............. A61B 5/00 600/301 |
| 2011/0034209 A1 | 2/2011 | Rubinsky et al. |
| 2011/0040197 A1* | 2/2011 | Welch ............... A61B 5/0205 600/509 |
| 2011/0257489 A1* | 10/2011 | Banet ................ A61B 5/0809 600/301 |
| 2013/0144136 A1* | 6/2013 | Rymut ............... A61B 5/0059 600/310 |
| 2013/0231947 A1* | 9/2013 | Shusterman ........ G06F 19/3443 705/2 |

OTHER PUBLICATIONS

Chung-Ping Young et al., "A portable multi-channel behavioral state and physiological signal monitoring system," May 13, 2012, pp. 2687-2691.

International Search Report and Written Opinion issued in International Application No. PCT/US2014/020903 dated Dec. 5, 2014.

* cited by examiner

| Index | Hgb | BUN | Cr | PVI | BP |
|---|---|---|---|---|---|
| Dehydration | ↑ | ↑ | ↑ | ↑ | → |

FIG. 8A

| Index | Hgb | BUN | Cr | PVI | BP |
|---|---|---|---|---|---|
| Renal Insufficiency | → | ↑↑ | ↑ to ↑↑ | → | ← |

FIG. 8B

| Index | Hgb | BUN | Cr | PVI | BP |
|---|---|---|---|---|---|
| Over-hydration | → | → | ↔ | → | ← |

| Index | Hgb | BUN | Cr | PVI | BP |
|---|---|---|---|---|---|
| Gastrointestinal Bleeding | → | ← | ↔ | ← | ↔ to → |

FIG. 8E (850)

| Index | Hgb | BUN | Cr | PVI | BP |
|---|---|---|---|---|---|
| Congestive Heart Failure Exacerbation | ↔ to → | ↔ to → | ↔ to ← | → | ↔ to ← |

FIG. 8F (860)

| Index | Chol | HDL | Chol/HDL | Trig | BP |
|---|---|---|---|---|---|
| Cardiovascular Risk | ← | → | ← | ← | ← |

| Index | Na+ | K+ | CO2 | Cl- | Glu | Ca | BUN | Cre | ALP | ALT | AST | Tbil |
|---|---|---|---|---|---|---|---|---|---|---|---|---|
| Diabetic Ketoacidosis | ↓ | ↕, mostly ↓ | → | → | ↑↑ | ↔ to ↓ | ↑ | ← | ↕ | ↕ | ↕ | ↕ |
| Asthma Exacerbation | ↕ | ↕ | ↕ | ↕ | ↕ | ↕ | ↕ | ↕ | ↕ | ↕ | ↕ | ↕ |
| Acute Upper Resp Infection | ↕ | ↕ | ↕ | ↕ | ↕ | ← | ↕ | ↕ | ↕ | ↕ | ↕ | ↕ |
| Chronic Renal Insufficiency | ↔ to ↓ | ← | ↔ to ↓ | ↔ to ↓ | ↔ to ↑ | ↕ | ↑↑ | ↑↑ | ↕ | ↑↑ | ↑↑ | ← |
| Liver Cirrhosis/Failure | ↔ to ↓ | ↕ | ↕ | ↔ to ↓ | ↔ to ↓ | ↕ | ↔ to ↓ | ↔ to ↑ | ↔ to ↑ | ↕ | ↕ | ↕ |
| Chronic Hypertension | ↔ to ↑ | ↔ to ↓ | ↕ | ↕ | | ↕ | ↕ | ↕ | ← | ↔ to ↑ | ↔ to ↑ | ↕ |
| Hyperlipidemia | ↕ | ↕ | ↕ | ↕ | ↕ | ↕ | ↕ | ↕ | ↕ | ↔ to ↑ | ↔ to ↑ | ↑↑ |
| Acute cholecystitis | ↕ | ↕ | ↕ | ↕ | ↕ | ↕ | ↕ | ↕ | ← | ↕ | ↕ | ↑↑ |
| Evolving MI | ↕ | ↕ | ↕ | ← | ↕ | ↕ | ↑↑ | ↕ | ↕ | ↔ to ↑ | ↔ to ↑ | ↕ |
| Dehydration/heat stroke | ← | ↔ to ↑ | ← | | | | | ← | | | | ↔ to ↑ |

| | Alb | TP | Chol | HDL | Trig | LDL | VLDL | SpO2 | BP | RR | Temp | ECG/HR |
|---|---|---|---|---|---|---|---|---|---|---|---|---|
| | ↕ | ↕ | ↕ | ↕ | ↑ or ↔ | ↕ | ↕ | ↔ to ↓ | → | ← | ↓ or ↑ | ← |
| | ↕ | ↕ | ↕ | ↕ | ↕ | ↕ | ↕ | → | ↔ to ↑ | ← | ← | ← |
| | ↕ | ↕ | ↕ | ↕ | ↕ | ↕ | ↕ | ↔ to ↓ | ← | ↑ or ↔ | ← | ↑ or ↔ |
| | → | → | ↔ to ↓ | ↔ to ↓ | ↔ to ↑ | ↔ to ↑ | ↔ to ↓ | ↕ | ↔ to ↑ | ↑ or ↔ | ↕ | ↔ to ↔, may see peaked T waves |
| | ↕ | ↕ | ← | ↔ to ↓ | ↕ | ← | ← | ↕ | ↑↑ | ↑ or ↔ | ↕ | varied depending on extent of disease |
| | ↕ | ↕ | ↕ | ↔ to ↓ | ↔ to ↑ | ↔ to ↑ | ↔ to ↑ | ↕ | ↔ to ↑ | ↕ | ← | LVH, possible evidence of old MI |
| | ↕ | ↕ | ↔ to ↑ | ↕ | ↔ to ↑ | ↕ | ↕ | ↕ | ↔ to ↑ | ↔ to ↑ | ↔ to ↑ | ↔, may see Q waves |
| | ↕ | ↕ | ↕ | | ↕ | | | ↔ to ↓ | ↔ to ↓ | ↔ to ↑ | ↔ to ↑ | ← |
| | ← | ← | | | | | | ↔ to ↓ | → | | | ↑, ST segment elevation, poor R wave progression |

FIG. 9

CLOUD-BASED PHYSIOLOGICAL MONITORING SYSTEM

PRIORITY CLAIM AND REFERENCE TO RELATED APPLICATIONS

The present application claims priority benefit under 35 U.S.C. § 119(e) to U.S. Provisional Patent Application Ser. No. 61/801,464, filed Mar. 15, 2013, titled Cloud-Based Blood Glucose Monitoring System; U.S. Provisional Patent Application Ser. No. 61/841,346, filed Jun. 30, 2013, titled Cloud-Based Monitoring System; U.S. Provisional Patent Application Ser. No. 61/885,491, filed Oct. 1, 2013, titled Cloud-Based Monitoring System; and U.S. Provisional Patent Application Ser. No. 61/922,861, filed Jan. 1, 2014, titled Cloud-Based Physiological Index Monitoring System; all of the above-referenced provisional patent applications are hereby incorporated in their entireties by reference herein.

BACKGROUND OF THE INVENTION

Medical device manufacturers are continually increasing the processing capabilities of physiological monitors that process signals based upon the attenuation of light by a tissue site. In general, such physiological monitoring systems include one or more optical sensors that irradiate a tissue site and one or more photodetectors that detect the optical radiation after attenuation by the tissue site. The sensor communicates the detected signal to a physiological monitor, which removes noise and preprocesses the signal. Advanced signal processors then perform time domain and/or frequency domain processing to determine blood constituents and other physiological parameters.

Manufacturers have advanced basic pulse oximeters from devices that determine measurements for blood oxygen saturation ("SpO$_2$"), pulse rate ("PR") and plethysmographic information to read-through-motion oximeters and to co-oximeters that determine measurements of many constituents of circulating blood. For example, Masimo Corporation of Irvine Calif. ("Masimo") manufactures pulse oximetry systems including Masimo SET® low noise optical sensors and read through motion pulse oximetry monitors for measuring SpO$_2$, pulse rate (PR) and perfusion index (PI). Masimo optical sensors include any of Masimo LNOP®, LNCS®, SofTouch™ and Blue™ adhesive or reusable sensors. Masimo pulse oximetry monitors include any of Masimo Rad-8®, Rad-5®, Rad®-5v or SatShare® monitors. Such advanced pulse oximeters and low noise sensors have gained rapid acceptance in a wide variety of medical applications, including surgical wards, intensive care and neonatal units, general wards, home care, physical training and virtually all types of monitoring scenarios.

Many innovations improving the measurement of blood constituents are described in at least U.S. Pat. Nos. 6,770,028; 6,658,276; 6,157,850; 6,002,952; 5,769,785 and 5,758,644, which are assigned to Masimo and are incorporated in their entireties by reference herein. Corresponding low noise optical sensors are disclosed in at least U.S. Pat. Nos. 6,985,764; 6,088,607; 5,782,757 and 5,638,818, assigned to Masimo and hereby incorporated in their entireties by reference herein.

Advanced blood parameter measurement systems include Masimo Rainbow® SET, which provides measurements in addition to SpO$_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Advanced blood parameter monitors further include Masimo Rainbow 4D™ DC sensors and Masimo Pronto® and Pronto-7® monitors for noninvasive and quick spot checking of total hemoglobin (SpHb®, SpO$_2$, pulse rate and perfusion index).

Advanced parameter measurement systems may also include acoustic monitoring such as acoustic respiration rate (RRa™) using a Rainbow Acoustic Sensor™ and Rad-87™ monitor, available from Masimo. An advanced parameter measurement system that includes acoustic monitoring is described in U.S. Pat. Pub. No. 2010/0274099, filed Dec. 21, 2009, titled Acoustic Sensor Assembly, assigned to Masimo and incorporated in its entirety by reference herein.

Innovations relating to other advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, Calif. (Cercacor) and all incorporated in their entireties by reference herein.

SUMMARY OF THE INVENTION

One aspect of a cloud-based physiological monitoring system is a sensor in communications with a living being so as to generate a data stream generally responsive to a physiological condition of the living being. A monitor receives the data stream from the sensor and transmits the data stream to a cloud server. The cloud server processes the data stream so as to derive parameters having values responsive to the physiological condition. The cloud server derives a medical index based upon a combination of the parameters. The cloud server communicates the medical index to the physiological monitor and the physiological monitor displays the medical index.

In an embodiment, the cloud-based physiological monitoring system sensor comprises an optical sensor and the parameters comprise a blood constituent parameter. The parameters comprise a plethysmograph waveform parameter. A blood pressure sensor is in communications with the living being, and a blood pressure monitor receives a blood pressure data stream from the blood pressure sensor and transmits the blood pressure data stream to the cloud server. The cloud server processes the blood pressure data stream so as to derive a blood pressure parameter having a blood pressure value responsive to the physiological condition and the parameters further comprise the blood pressure parameter.

In various other embodiments, the medical index is based upon trends of the combination of the parameters. The blood constituents include Hgb, BUN and Cr. The medical index relates to at least one of hydration, cardiovascular risk and renal insufficiency. In a particular embodiment, the medical index relates to at least one of dehydration, over hydration, gastrointestinal bleeding and congestive heart failure exacerbation.

Another aspect of a cloud-based physiological monitoring system comprises generating sensor data generally responsive to a physiological phenomenon of a living being, communicating the sensor data to a local medical device and transmitting the sensor data from the local medical device to a remote cloud server. The system further comprises processing the sensor data at the cloud server so as to derive parameters having values responsive to the physiological phenomenon and trending the parameters at the cloud server so as to derive a medical index responsive to the parameters, where the medical index indicates a medical condition. The system additionally comprises communicating the medical index to the local medical device and displaying the medical index on the local medical device.

In various embodiments, cloud-based physiological monitoring system comprises generating second sensor data generally responsive to a second physiological phenomenon of a living being, communicating the second sensor data to a second local medical device and transmitting the second sensor data from the second local medical device to the remote cloud server. The system further comprises processing the second sensor data at the cloud server so as to derive a second parameter having values responsive to the second physiological phenomenon and trending the second parameter with at least one of the parameters at the cloud server so as to improve the efficacy of the medical index. In various other embodiments, generating sensor data comprises optically-deriving data responsive to pulsatile blood flow. Generating second sensor data comprises air-cuff-deriving data responsive to blood pressure. The system further comprises time frame matching the sensor data and the second sensor data at the cloud server. In a particular embodiment, displaying the medical index comprises indicating hydration on a smart cellular telephone.

A further aspect of a cloud-based physiological monitoring system comprises a physiological monitor in remote communications with a cloud server, where the physiological monitor inputs sensor data responsive to a physiological condition of a user. The cloud server is in remote communications with the physiological monitor so as to upload the sensor data. The cloud server executes signal processing algorithms so as to derive a physiological parameter from the sensor data. The cloud server downloads the physiological parameter to the physiological monitor for display to user.

In various embodiments, the physiological monitor has an online application that executes if the cloud server is available and, if so, the online application inputs sensor data from a physiological sensor in communications with the physiological monitor, transmits the sensor data to the cloud server, receives a parameter value that the cloud server derives from the sensor data and displays the parameter value on the physiological monitor. The physiological monitor has an offline application that executes if the cloud server is unavailable and, if so, the offline application inputs sensor data from a physiological sensor in communications with the physiological monitor, calculates a parameter value from the sensor data and displays the parameter value on the physiological monitor.

In various further embodiments, the online application performs an initial blood glucose calibration phase of the physiological monitor that comprises repeated blood sample data derived from a strip reader over an initial calibration period of several weeks and repeated optical sensor data corresponding to the blood sample data. The blood sample data and the sensor data are transmitted to the cloud server and the cloud server correlates the blood sample data and the sensor data during the initial calibration stage. The online application further performs an end blood glucose calibration phase of the physiological monitor that comprises optical sensor data occasionally interspersed with blood sample data. The sensor data and occasional blood sample data are transmitted to the cloud server, which updates the calibration as needed.

In additional embodiments, a share user establishes a receive user who is allowed to view the share user's medical information. A share ID is associated with the share user's physiological monitor. A receive ID is associated with the receive user's physiological monitor. The cloud server associates the share ID with the receive ID. The cloud server encrypts the share user's medical information according to a share key based upon the share ID. The cloud server generates a decryption key based upon the receive ID. The cloud server transmits the encrypted medical information and share key to the share user. The cloud server transmits the receive key to the receive user. The share user posts the encrypted medical information to a public website, the receive user downloads the encrypted medical information and the receive user decrypts the medical information using the receive key.

BRIEF DESCRIPTION OF THE DRAWINGS

FIG. 8A-F are medical index tables illustrating trends in blood-related parameters, plethysmograph waveform features and blood pressure that are indicative of dehydration, renal insufficiency, over-hydration, gastrointestinal bleeding, congestive heart failure exacerbation and cardiovascular risk, respectively.

FIG. 9 is a comprehensive medical index table illustrating trends in various physiological measurements, including blood-constituents and oxygen saturation, blood pressure, respiration rate (RR), temperature and heart-related parameters including heart rate (HR) and electrocardiogram (ECG) waveform features indicative of various physiological conditions, maladies and diseases.

DETAILED DESCRIPTION OF THE PREFERRED EMBODIMENTS

Figure 1A:
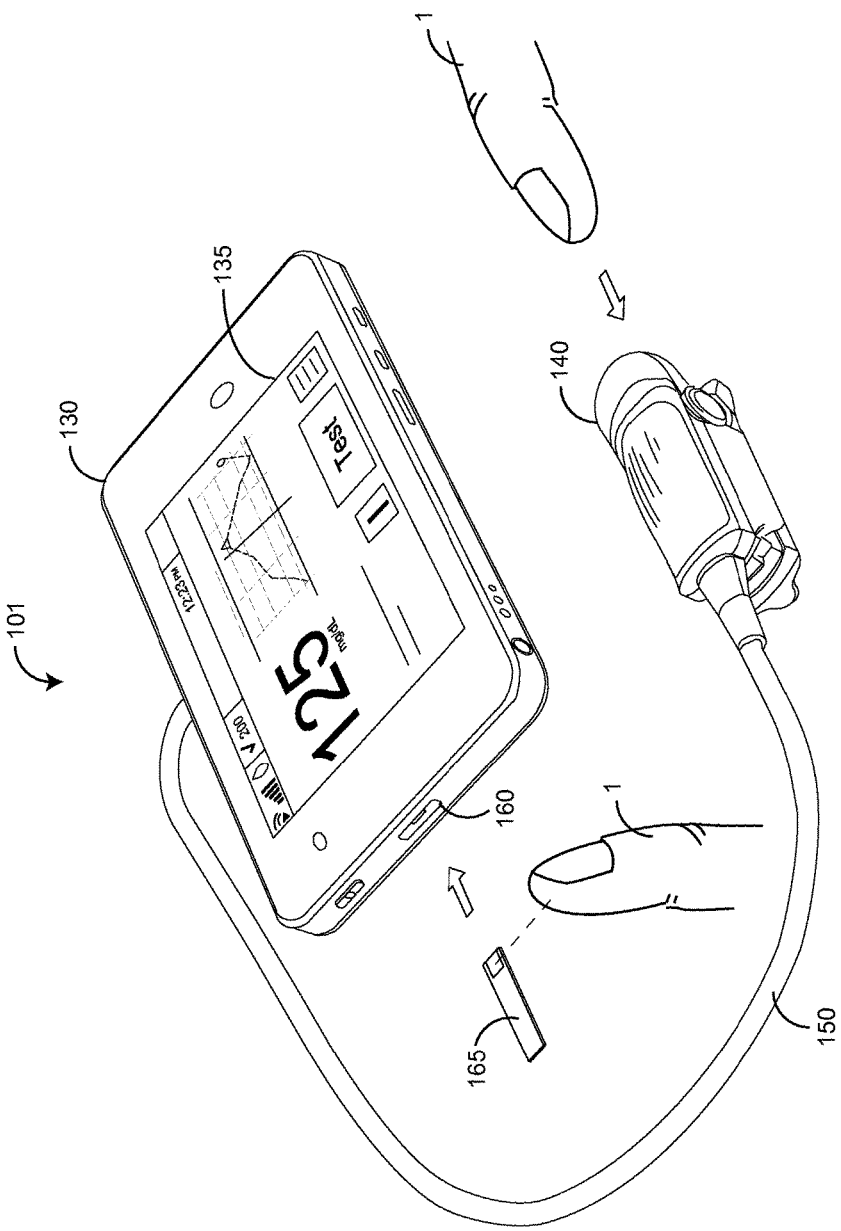
FIGS. 1A-B are perspective views of cloud-based monitoring systems that are capable of blood parameter and blood pressure monitoring.
Figure 1B:
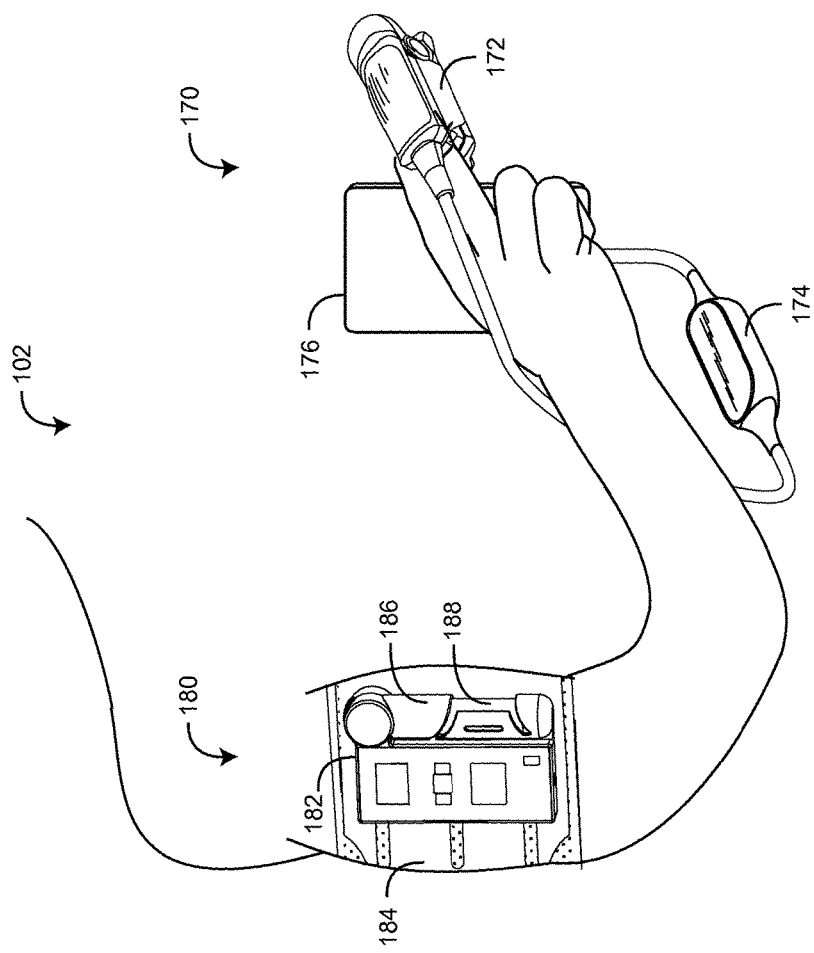

FIGS. 1A-B illustrate cloud-based physiological monitoring systems that are capable of blood parameter, blood pressure and other physiological measurements. As shown in FIG. 1A, a physiological monitoring system 101 advantageously provides spot check measurements of various blood constituents, such as blood glucose. The monitoring system 101 has a blood parameter monitor 130, an optical sensor 140, a sensor cable 150 electrically and mechanically interconnecting the monitor 130 and sensor 140 and a monitor-integrated test strip reader 160 that accepts test strips 165 via a test strip slot. In a particular use, the monitoring system 101 provides relatively frequent noninvasive measurements of blood glucose interspersed with relatively infrequent invasive measurements of blood glucose so as to manage individual blood glucose levels. The monitoring system 101 individually calibrates the sensor 140 measurements with intermittent test strip measurements to advantageously provide the accuracy of individualized glucose test strip measurements at a much-reduced frequency of blood draws. Reduced blood draws are a substantial aid to persons who require frequent monitoring of blood glucose levels to manage diabetes and related diseases. In an embodiment, the monitor 130 has a handheld-tablet housing including an integrated 5.6 in IPS touch screen 135 defining one or more input keys and providing a display of blood glucose levels among other features. The monitor 130 advantageously has Wi-Fi and 3G cellular communications for cabled and wireless cloud access. Cloud connectivity allows remote sensor data processing, algorithm development, individual blood glucose calibration and software updates among other cloud services. A blood parameter monitoring system is described with respect to U.S. patent application Ser. No. 13/646,659, filed Oct. 5, 2012, titled Noninvasive Blood Analysis System and U.S. patent application Ser. No. 13/726,539, filed Dec. 24, 2012, titled Blood Glucose Calibration System, both assigned to Cercacor and both incorporated in their entireties by reference herein.

As shown in FIG. 1B, a physiological monitoring system 102 may have two or more monitors 170, 180 in sensor communications with an individual person so as to generate multiple sensor data streams and display multiple types of physiological parameters. In an embodiment, the multiple monitors 102 include a handheld blood parameter monitor 170 and a arm cuff-mounted blood pressure monitor 180. In an embodiment, the handheld blood parameter monitor 170 has an optical sensor 172, a monitor module 174 and a handheld smart cellular telephone ("smart phone") 176. An optical sensor is described above with respect to FIG. 1A. The optical sensor attaches to a fleshy tissue site, such as a fingertip. The monitor module 174 drives LEDs in the optical sensor 172 and receives detector signals responsive to the LED emitted light after attenuation by the fleshy tissue and blood flow within the fleshy tissue. The blood flow may be active-pulsed and arterial-pulse blood flow. The monitor module 174 receives the detector signals, i.e. the raw sensor data stream and derives physiological parameters, which are communicated to the smart phone 176. This alleviates the smart phone 176 from the computationally-intense task of processing raw sensor data and deriving physiological parameters, which the current generation of smart phones are ill-equipped to perform. A combination optical sensor, monitor module and smart phone configured as a mobile physiological monitor are described in U.S. patent application Ser. No. 14/033,315, titled Physiological Monitor with Mobile Computing Device Connectivity, assigned to Cercacor and incorporated in its entirety by reference herein.

Also shown in FIG. 1B, in an embodiment, a cuff-mounted, blood pressure monitor 180 is attached to a person's limb so as to measure blood pressure parameters. The blood pressure monitor 180 has a monitor module 182, an inflatable cuff 184 and a gas chamber 186. The monitor module 182 is mounted to the inflatable cuff 184, is battery-operated and includes a display and a user interface. In an embodiment, the gas chamber 186 is configured for disposable $CO_2$ cartridges 188 in communications with a monitor-controlled gas valve for automatic cuff inflation. Also shown in FIG. 1B, the blood pressure monitor 180 has an OLED display, a 16 g $CO_2$ canister 188 for automatic cuff information, and Bluetooth and USB communication interfaces. Sensor capabilities include systolic and diastolic blood pressure parameters, pulse rate and mean arterial pressure (MAP). The blood pressure monitor 180 also has cloud communications capabilities either directly via a wireless wide area communications link or via local area communications (e.g. Wi-Fi, Bluetooth) with other devices that have such a wide area link, such as the smart phone 176. A cuff-mounted monitor is described in detail in U.S. patent application Ser. No. 13/838,225, filed Mar. 15, 2013, titled Patient Monitoring System, assigned to Cercacor and incorporated in its entirety by reference herein. These cloud-based physiological monitors 101-102 (FIGS. 1A-B) advantageously provide measurement capabilities for more than a dozen different noninvasive parameters in addition to cloud services including clinical data visualization, storage and exchange and real-time algorithm processing.

Further shown in FIG. 1B, a multiple-monitor configuration 102 can advantageously derive multiple sensor 170, 180 data streams and multiple physiological parameters from the same individual and communicate these data streams and parameters to the cloud, as described in further detail with respect to FIGS. 2-7, below. This advantageously allows a cloud-based processor to receive two or more independent sensor data streams, for example data from a blood pressure sensor and an optical sensor attached to an individual, and derive cross-sensor parameters such as the medical indices described below. Such cross-sensor parameters allow caregivers to assess a broader spectrum of physiological conditions from states and trends in these cross-sensor parameters than possible with a data stream from a single sensor.

Although a multiple-monitor configuration 102 is described above with respect to a blood pressure sensor and an optical sensor, each in communications with their individual monitors, in other embodiments, multiple sensors may be in communications with a single monitor. These sensors may include a variety of devices including accelerometers for data regarding body position and activity; body and environment temperature sensors; electrical sensors for deriving EEG, EKG data streams; acoustic sensors for detecting respiration and other body sounds; and capnography sensors for monitoring carbon dioxide, among others.

Additionally shown in FIG. 1B, in an embodiment, individual monitors 170, 180 may each communicate directly to the cloud utilizing wide area communications, such as wired or wireless Internet or cellular network devices. In an embodiment, a first monitor 170 may have wide area communications capability, and a second monitor 180 may use local area communications to communicate its sensor data to the first monitor 170 for transmission to a cloud-based processor. In another embodiment, first 170 and second 180 monitors may each use local area communications to communicate sensor data to a local processing device, such as a laptop or desktop computer that, in turn, uses wide area communications to communicate with a cloud-based processor. Various monitor-cloud data communications and processing scenarios are further described with respect to FIGS. 2-7, below.

Figure 2:
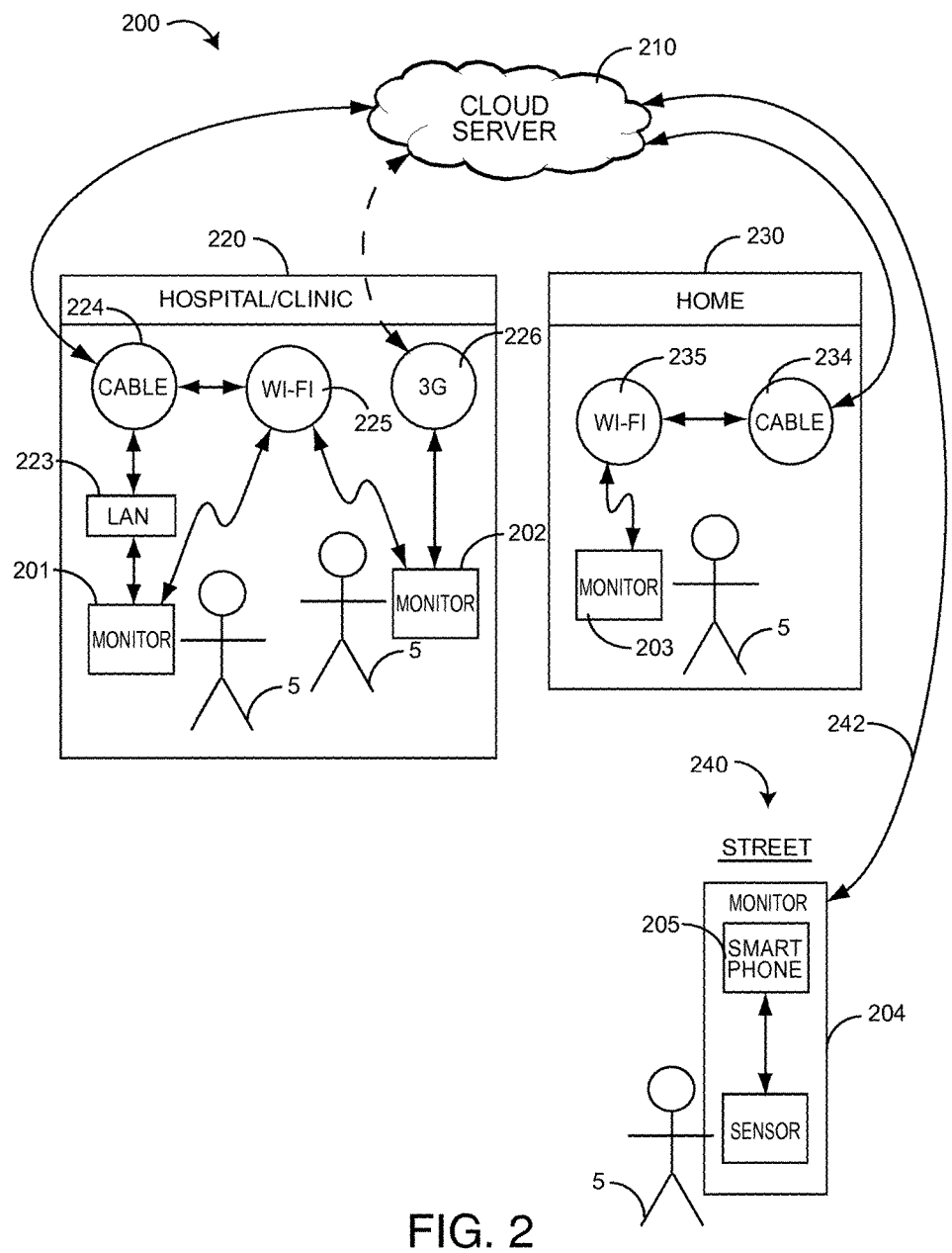
FIG. 2 is a general flow diagram of a cloud-based monitoring system.

FIG. 2 illustrates a cloud-based monitoring system 200 having a cloud server 210 in communications with physiological monitors 201-204, such as described with respect to FIGS. 1A-B, above. The monitors 201-204 are located in various hospital/clinic 220, home 230 and street 240 locations remote from the cloud server 210. In an embodiment, the cloud server 210 utilizes various sensor signal processing algorithms to estimate physiological parameters such as blood oxygen saturation, carboxyhemoglobin, methomoglobin, blood glucose, total hemoglobin and respiration rate, to name just a few. These parameters are derived from sensor data collected by the monitors 201-204 and transmitted to the cloud server 210 via various data transmission paths.

As shown in FIG. 2, data is transmitted from monitors 201-204 to the cloud server 210 via wired (e.g. LAN 223) or wireless (e.g. Wi-Fi 225) local networks to wide area media, such as Internet cable 224 or telecommunications (e.g. 3G 226) networks. Alternatively, a monitor 204 may have a wireless link 242 for direct data transmission to the cloud over a cellular network. These wide area media, in turn, are in communications with the cloud server 210, which calculates physiological parameters as described above. The calculated parameters are transmitted back to the monitors 201-204 or smart phone 205 for display, additional processing and storage of physiological parameters as well as corresponding notification and use by patients and their care providers.

Further shown in FIG. 2, the above-described configurations allow all monitors 201-204 to benefit from the same set of signal processing algorithms residing in the cloud server 210. At the same time, these signal processing algorithms can remain proprietary and protected from reverse engineering in the event any monitors 201-204 are lost or stolen, as the monitors 201-204 do not have access to the cloud algorithms. In particular, the monitors 201-204 only have access to raw (sensor) data, error messages and data pre-processing (e.g. for probe-off detection). In other embodiments, non-proprietary signal processing algorithms are resident in the monitors 201-204 and proprietary algorithms are resident in the cloud 210. In an embodiment, a dual communications channel between one or more monitors 201-204 and the cloud 210 may be implemented for redundancy, so as to resolve safety issues related to critical medical information and potential communication or monitor malfunctions. For example, a direct 3G (telecommunications) link between a monitor 201-204 and the cloud server 210 may be available as backup to landline communications.

Figure 3:
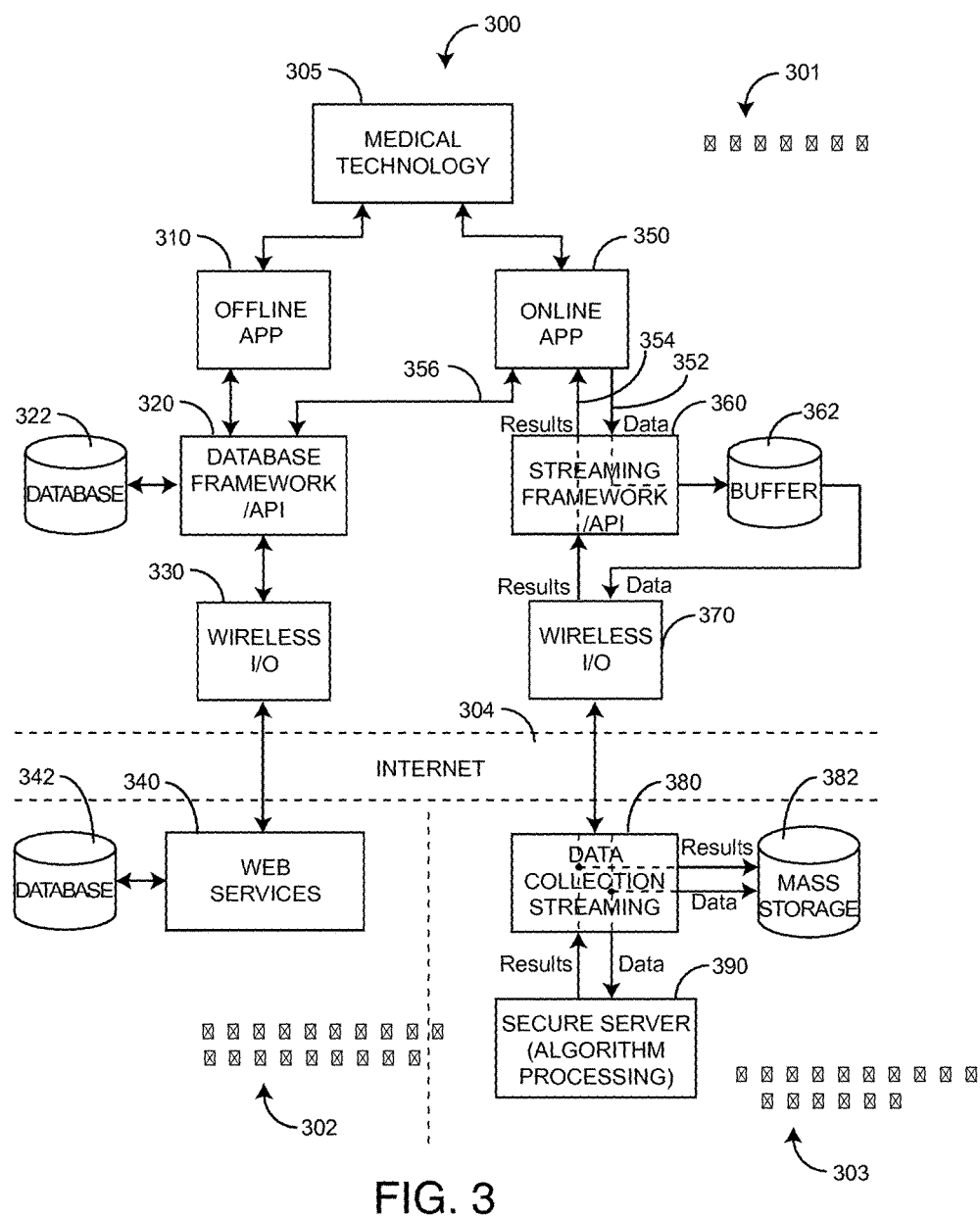
FIG. 3 is a detailed block diagram of a cloud-based monitoring system.

FIG. 3 illustrates a cloud-based physiological monitoring system 300 including a monitor 301, a monitoring community 302 and a monitoring center 303. A monitor 301 is in communications with one or more sensors, as described with respect to FIGS. 1A-B, above. In an embodiment, the monitor 301 includes medical technology 305 in addition to non-medical computer and telecommunication functions such as are available on any of various mobile consumer devices (not shown). Medical technology 305 includes both an offline application 310 and an online application 350 for measuring and managing blood glucose, blood pressure and other physiological parameters and medical indices.

As shown in FIG. 3, following successful calibration, the offline application 310 allows a patient to attach a sensor, e.g. 140 (FIG. 1A), push a monitor button, e.g. "Test," and initiate a sampling of sensor data and derivation of physiological parameters, such as blood glucose, utilizing resident processors and algorithms. The monitor 301 then displays the resulting physiological parameter value on a monitor display, e.g. 135 (FIG. 1A). The only "cloud" function the offline app 310 performs is to occasionally dump patient data, including derived physiological parameters and related information, from its database 322 to, say, a treating physician's database 342, so that the physician can monitor and review the patient's disease management and insure that the monitor and sensor are functioning normally. This feature also allows a patient to share their medical information with other members of the monitoring community 302, including family members or non-related persons having similar treatments and therapies, as described with respect to FIG. 5, below.

Also shown in FIG. 3, an online application 350 advantageously transmits the monitor 301 sensor data via the cloud (e.g. Internet 304) to the monitoring center 303, which is remote from the monitor 301 location. Physiological parameter processing algorithms reside in a secure server 390, which derives blood glucose values, other blood constituent values and measurements of other physiological parameters, such as blood pressure, with very small latency times. A data buffer 362 in the monitor 301 reduces transmit data latency times. The calculated physiological parameter results are immediately returned to the monitor 301 for display.

Further shown in FIG. 3, the monitoring center 303, which is accessed via the online application 350, has more processing power and is easier to maintain than the offline application 310. In particular, algorithm 390 modifications and upgrades can be made simply and quickly at the monitoring center 303 site as compared to upgrades across many monitors 301 distributed over disparate locations. Further, the monitoring center 303 processors have significantly greater computational capabilities than the relatively limited processors residing in each monitor 301. Also, algorithms developed at the monitor manufacturer's facility typically have to be reduced in size and ported to a different programming language for installation in each monitor 301, which requires speed and memory size tradeoffs that are nonexistent at the monitoring center 303. In addition, the processor intensive computations required for offline applications raise heat dissipation issues for relatively compact handheld and tablet monitors. The downside of the monitoring center 303 is the necessity of reliable connectivity to all of the monitors 301.

According to the trade-offs described above, in a particularly advantageous embodiment, the online application 350 is utilized for cloud computing of all physiological parameters or at least the most computationally intense parameters unless cloud access is temporarily unavailable. In the event the monitoring center 303 processors are down or the online application 350 communications link with the monitoring center 303 is lost, then the offline application 310 performs the necessary computations. This can be done in an emergency for a few minutes without concern about monitor 301 heat dissipation limitations. Further, for blood glucose measurements, loss of cloud access is mitigated somewhat by the device strip reader 160 (FIG. 1A), which is always available to users in the event the monitoring center 303 is "down" or when a particular monitor 301 has no cloud access.

In a particularly advantageous blood glucose management embodiment, the offline application 310 has a setting for the maximum time allowed between invasive (test strip) measurements of blood glucose. The offline application 310 tracks the time that has elapsed since the last test strip measurement was made and disables noninvasive blood glucose monitoring if that elapsed time limit is exceeded. In an embodiment, the offline application 310 provides a user one or more warning messages of an impending noninvasive measurement timeout due to an excessive elapsed time from the last invasive measurement. In an embodiment, either the offline application 350 or the online application 310 may adjust the maximum time allowed between invasive measurements as a function of the delta time and the delta blood glucose values between two consecutive invasive measurements. This maximum elapsed time adjustment advantageously takes into account relatively small changes, historically, in invasive glucose values over relatively long time spans so as to lengthen the maximum-allowed elapsed time between invasive measurements. Likewise, the maximum elapsed time adjustment takes into account relatively large changes, historically, in invasive glucose values over relatively short time spans so as to shorten the maximum-allowed elapsed time between invasive measurements.

Figures 4A, 4B:
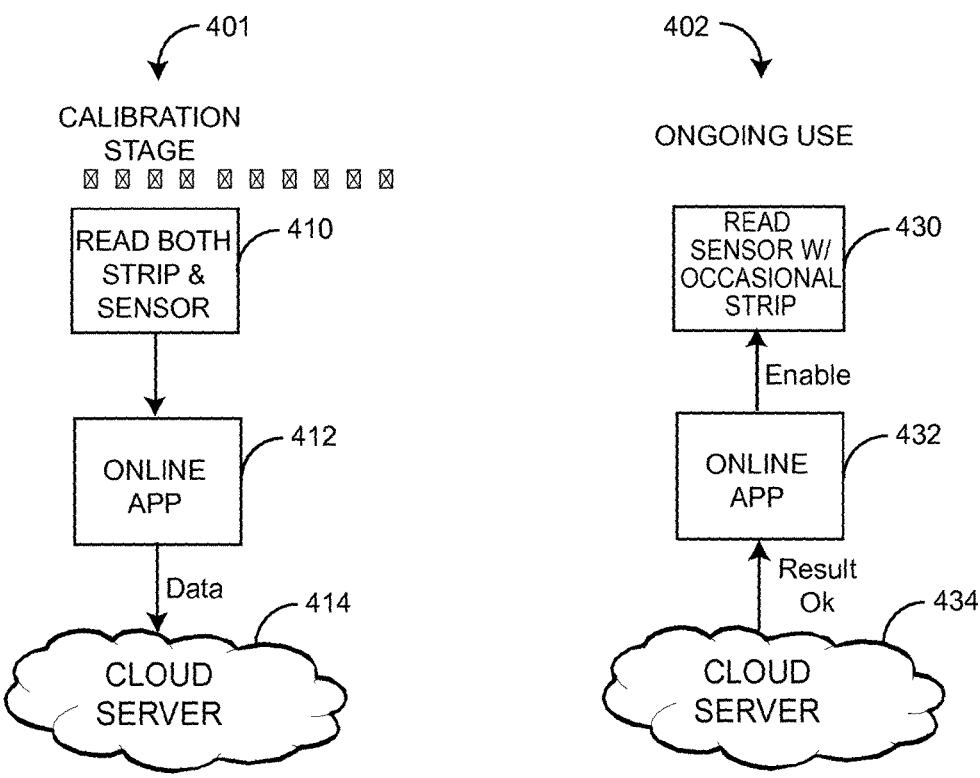
FIGS. 4A-B are general flow diagrams of blood glucose calibration.

FIGS. 4A-B illustrate a blood parameter calibration process 401-402 that includes set-up and calibration functions for a cloud-based physiological monitor, such as described with respect to FIGS. 1-3, above. FIG. 4A illustrates an initial calibration stage 401 when a new user attempts to calibrate their monitoring system, e.g. 101 (FIG. 1A) using a strip reader 160 and test strip 165 (FIG. 1A). At regular intervals, blood samples are read with a strip at the same time that optical sensor 140 (FIG. 11) data is taken 410. An online application 412 sends the strip and sensor data to a cloud server 414. See, e.g., 303, 350 (FIG. 3). The strip readings are then compared to calculations based upon optical sensor 140 (FIG. 1A) measurements. If there are consistent matches between the invasive and noninvasive measurements, the calibration stage 401 is complete. If not, the calibration stage 401 continues. This process may take 1 to 6 weeks and, in some cases, may not be successful. That is, after some predetermined number of measurements or calibration time interval, the strip readings may not correlate with the optical sensor-based measurements. As a result, that particular individual is deemed not suitable for noninvasive glucose monitoring. FIG. 4B illustrates an ongoing use 402 once the user is initially calibrated 401. The cloud server 434 indicates to the online application 432 that the user is calibrated 401. The monitoring system 101 (FIG. 1A) is enabled accordingly 430 to use sensor-based measurements with occasional strip measurements to insure up-to-date calibration. This calibration process 401, 402 is particularly advantageous with respect to calibrating a cloud-based physiological monitor for noninvasive (optical sensor) blood glucose measurements interleaved with occasional invasive (glucose test strip) measurements.

Figure 5:
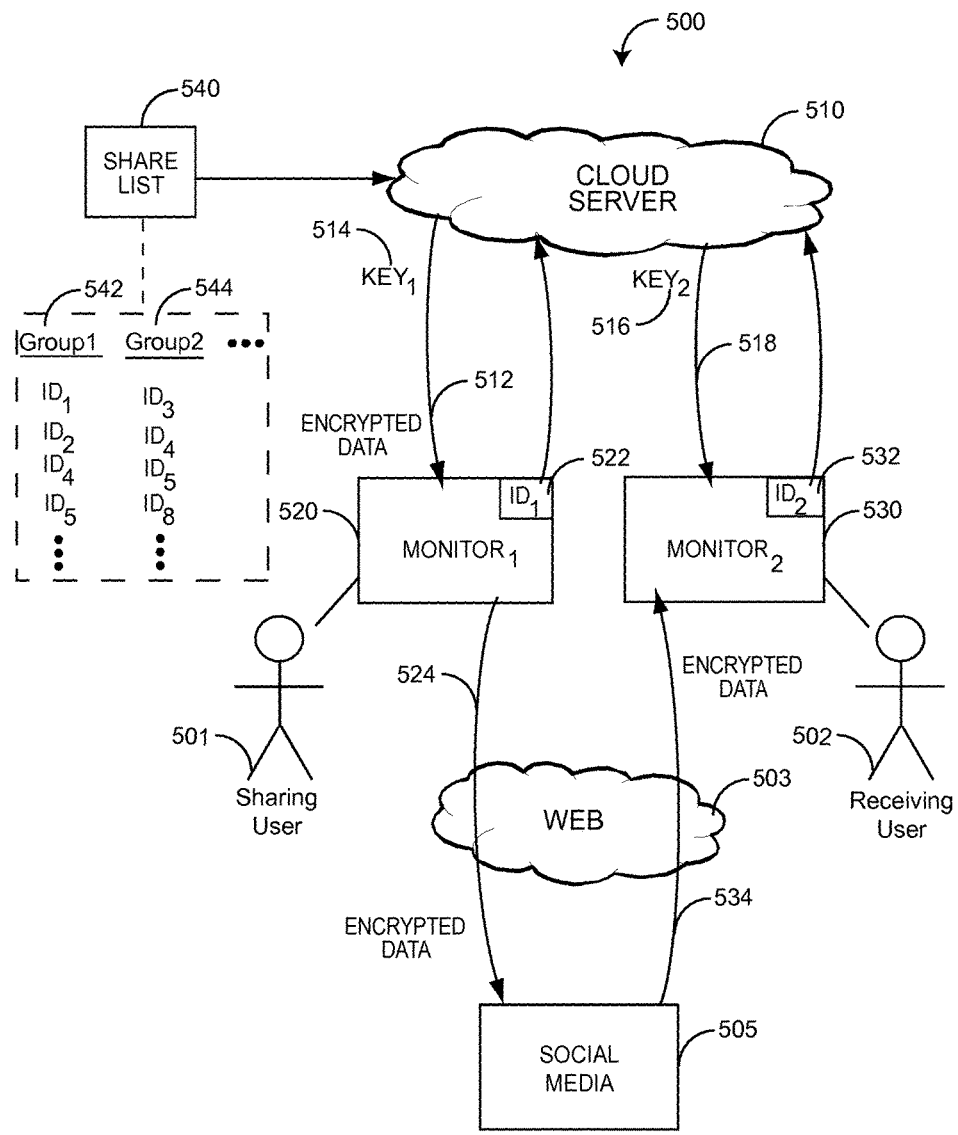
FIG. 5 is a general flow diagram of a cloud-based, protected social network for sharing monitoring measurements.

FIG. 5 illustrates a cloud-based, secure social network 500 that enables a monitor 101-102 (FIGS. 1A-B) user to confidentially share their medical information with a trusted group of other users. Medical information may include measured physiological parameters and a user's health management experiences. For example, medical information may be a past history of blood glucose measurements; steps taken to control blood glucose, including medication, diet and exercise; and recent blood glucose measurement results. The social media 505 for sharing this medical information may be any of the popular social media sites, such as Facebook or Google+, to name a few. The protected social network 500 incorporates cloud-based monitors 520, 530 in communications with a cloud server 510, as described with respect to FIGS. 1-4, above.

As shown in FIG. 5, each sharing user 501 communicates with the cloud server 510 so as to establish a share list 540 of one or more groups 542, 544 of receiving users 502 who are allowed to view the sharing user's medical information. Receiving user groups 542, 544 may be based upon, or restricted by, the type and scope of medical information shared. Each user 501, 502 is advantageously identified according to their monitor device ID 522, 532, which is securely registered with the cloud server 510. That is, one advantage of a cloud-based secure social network 500 is that only individuals assigned a monitor 520, 530 can belong, and membership in and use of the protected social network 500 is enforced by the cloud server 510 and its recognition of monitor IDs 522, 532. Accordingly, a sharing user's share list 540 securely establishes monitors 530 that receive monitoring data and other personal information regarding the sharing user 501.

Also shown in FIG. 5, the cloud server 510 advantageously manages encryption of share data according to the sharing user 501 and their share list 540. The cloud server 510 collects and stores monitoring device 520 data and calculates and stores corresponding measurement results, which may include share data. The cloud server 510 encrypts share data 512, which is transmitted from the cloud to the sharing user's monitor 520. A corresponding $KEY_1$ 514 based upon the sharing user's monitoring device $ID_1$ 522 is also transmitted to the sharing user's device 520. This allows the sharing user 501 to decrypt and view share data. A separate $KEY_2$ 516 is transmitted to a monitor 530 corresponding to a receiving user 502 listed on the share list 542. The cloud server 510 generates $KEY_2$ 516 according to the receiving user's device $ID_2$ 532.

Further shown in FIG. 5, the sharing user 501 can post the encrypted share data 524, at their discretion, to social media 505 of their choosing. A receiving user 502, at their discretion, can upload the encrypted data 534 and use their device specific $KEY_2$ 516 to decrypt and view the share data. Advantageously, the cloud server 510 in this secure data sharing architecture does not require a customized data sharing website and the corresponding setup and site management burdens. Cloud server 510 overhead is limited to share list 540 management, data encryption and key generation and encrypted data and key distribution based upon an existing network of monitors 520, 530 with registered and readable device IDs 522, 532.

Figure 6:
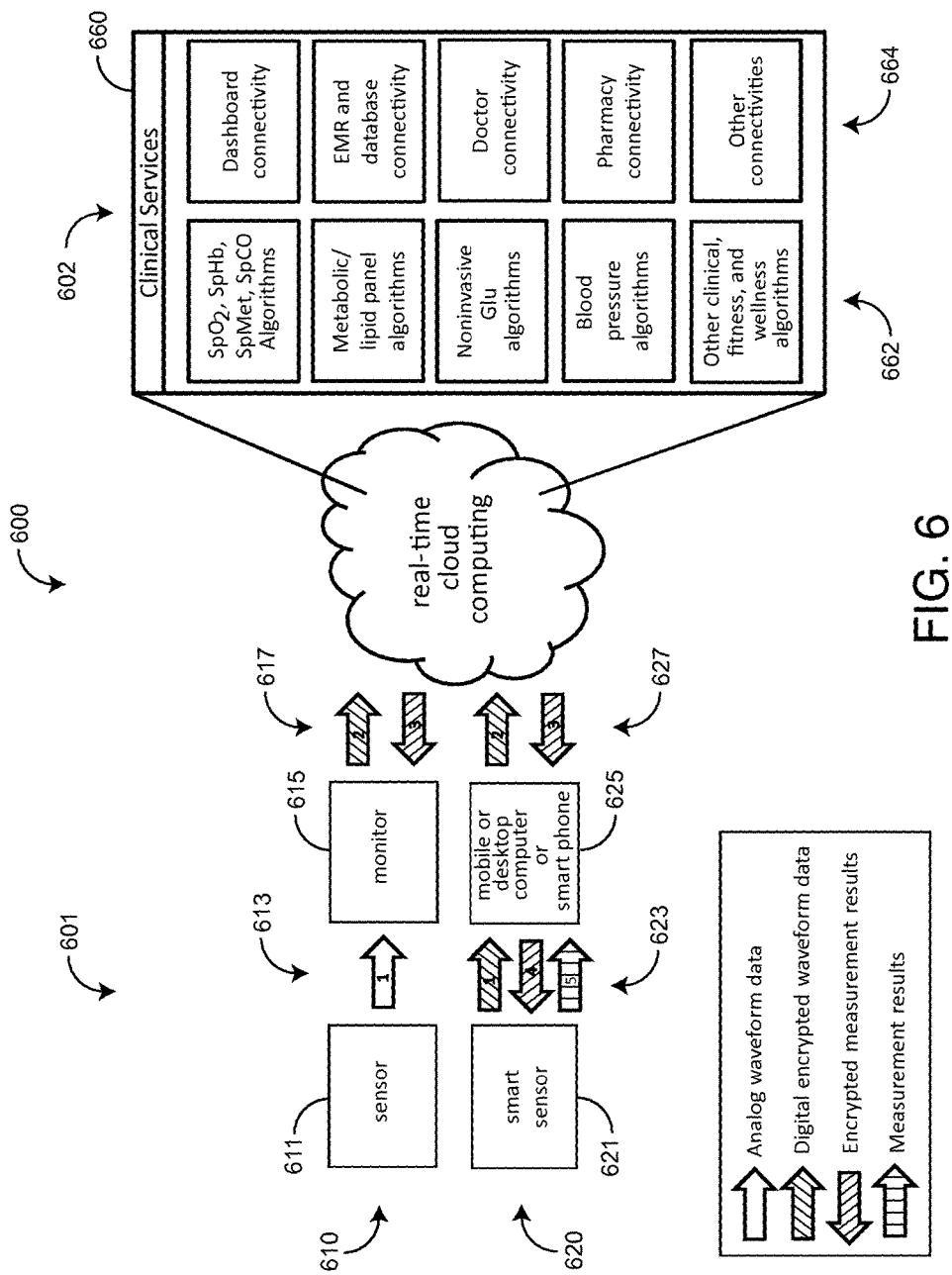
FIG. 6 is a general flow diagram of real-time algorithm processing using one or more of a sensor and connected medical device or a smart sensor and connected mobile or desktop device in communications with a cloud service so as to perform clinical services including physiological parameter calculations.

FIG. 6 illustrates a real-time cloud computing architecture 600. On a user side 601, various physiological monitoring systems 610, 620 exist in perhaps widespread geographical locations and disparate environments. In contrast, a centralized cloud server 602 provides a variety of clinical services 660 for these monitoring systems 610, 620. In an embodiment, various users each possess a physiological monitoring system 610 having a sensor 611 and a corresponding monitor 615, such as described with respect to FIG. 1A, above. The sensor 611 generates an analog data stream 613 responsive to at least some aspect of the user's physiology. The monitor 615 receives and processes the analog data stream 613 and generates an digital encrypted data stream 617 responsive to the sensor 611. For example, the data stream 617 may be optical sensor data that has been filtered, digitized, amplified, demodulated and decimated in the monitor 615 and then encrypted and transmitted to the cloud server 602.

As shown in FIG. 6, in an embodiment, various other users each possess a physiological monitoring system 620 having a smart sensor 621 and a corresponding smart phone 625, such as described with respect to FIG. 1B, above. (A mobile or desktop computer 625 may be used in lieu of a smart phone). The smart sensor 621 generates an analog data stream 613 responsive to at least some aspect of a user's physiology. A monitor module integral to the smart sensor 621 receives and processes the analog data stream and generates a digital encrypted data stream 623 responsive to the analog data stream. The smart phone 625 receives the digital encrypted data stream 623 and transmits it directly to the cloud server 602.

Also shown in FIG. 6, clinical services performed in the cloud 602 include algorithm computations 662 and connectivity 664. Algorithms 662 include those for calculating $SpO_2$, SpHb, SpMet and SpCO; metabolic and lipid parameters; noninvasive blood glucose parameters; blood pressure parameters and other clinical, fitness and wellness-related parameters. Connectivity 664 includes dashboard, EMR and database, doctor and pharmacy connectivities. The cloud 602 returns encrypted measurement results 627 to the monitor 615 or the smart phone 625. The smart phone 625 passes the encrypted measurement results 623 to the smart sensor 621, and the smart sensor 621 sends the (decrypted) measurement results 623 back to the smart phone 625.

The advantages of real-time medical parameter computing via the cloud 602 is flexibility, scalability and ease of maintenance of the algorithm portfolio. In addition, the cloud offers significant IP protection for these algorithms because algorithms are not calculated within a device exposed to hands-on reverse engineering. The disadvantages are that medical parameter cloud computing requires highly reliable connectivity combined with patient risk mitigation if such connectivity is lost.

Figure 7:
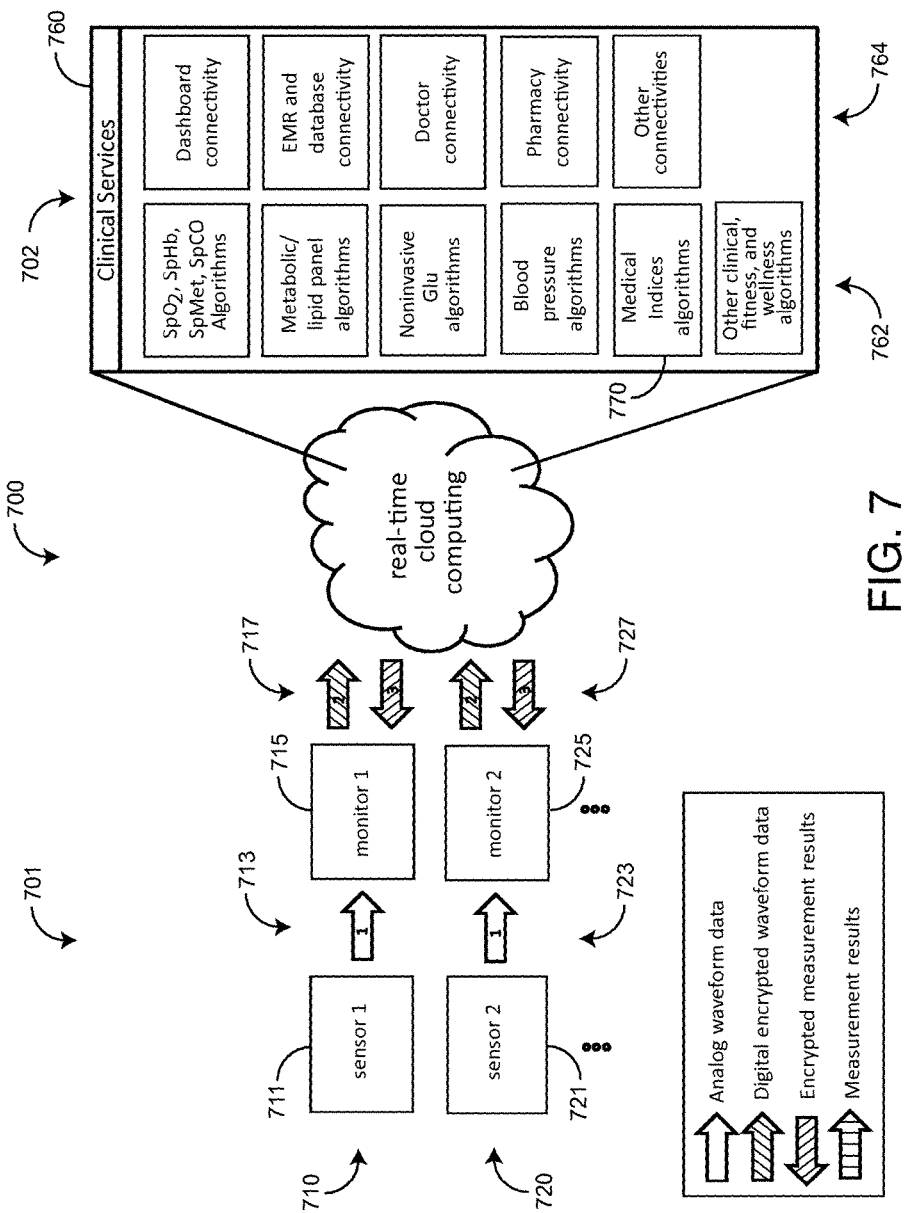
FIG. 7 is a general flow diagram of real-time algorithm processing using multiple sensors and connected medical devices in communications with a cloud service so as to perform clinical services including calculations of medical indices.

FIG. 7 illustrates another real-time cloud-computing architecture 700. In particular, multiple sensors 711, 721 in conjunction with corresponding monitors 715, 725, such as described with respect to FIGS. 1A-B, above, provide clinical services 760 via real-time cloud computing. Clinical services 760 performed in the cloud include the calculation of one or more blood constituents and blood pressure. Blood constituent calculations include oxygen saturation, normal and abnormal hemoglobin, metabolic and lipid constituents and glucose, as described with respect to FIG. 6, above. Also as described with respect to FIG. 6, above, data flow for a sensor 711, 721 and connected monitor 715, 725 includes analog waveform data from the sensor 711, 721 to the connected monitor 715, 725; digital encrypted waveform data to the cloud 717,727, which returns encrypted measurement results 717,727 to the monitor 715, 725.

As shown in FIG. 7, clinical services 760 further include calculation of medical indices 770, each of which are combinations of physiological parameters. As such, two or more monitors 715, 725 independently generate encrypted waveform data 717, 727 used to derive a medical index 770. The cloud 760 time synchronizes this data accordingly. In an embodiment, each device has a master clock so as to record a universal time. The cloud server 702 corrects for time differences and delays among devices that are part of the same user account. As an example, a user acquires a smart sensor/smart phone 170 (FIG. 1B) and a cuff-based blood pressure monitor 180 (FIG. 1B). The user registers these devices via their cloud account. After that, when measurements are taken, the cloud server 702 verifies if the set of required parameters are available for a particular medical index 770 and if the parameters were measured within the required time frame for these parameters.

As an example, blood pressure constantly varies. Therefore, when calculating an index involving other parameters, any measurement time frame mismatch should be small (a few minutes). In contrast, total cholesterol changes very slowly, and therefore the measurement time frame mismatch with respect to other parameters can be much larger (hours). If any time frame mismatch between measured parameters for a particular medical index is within tolerance, the cloud server 702 processes and displays the index on at least one of the user's monitors 715, 725. If a time frame mismatch is too large, then each of the monitor 715, 725 displays are dashed out for that index.

FIGS. 8A-F illustrate medical indices 800 based upon trends in some or all of selected blood constituents, e.g. Hgb (hemoglobin), BUN (blood urea nitrogen) and Cr (creatinine); plethysmograph waveform features, e.g. plethysmograph variability index (PVI) and blood pressure (BP) that are indicative of dehydration 810, renal insufficiency 820, over-hydration 830, gastrointestinal bleeding 840, congestive heart failure exacerbation 850 and cardiovascular risk 860, respectively. Specifically, if a monitor and sensor are only capable of, or enabled to, measure blood constituent parameters, then a particular medical index ("index") may be based exclusively upon, say, Hgb, BUN and Cr. If a monitor and sensor are also capable of, or enabled to, measure plethysmograph waveform features, then that index may be based upon Hgb, BUN, Cr and PVI. (See, e.g. FIG. 1A). Further, if one or more monitors/sensors attach to a person, then that index may be based upon Hgb, BUN, Cr, PVI and BP. (See, e.g. FIG. 1B). A plethysmograph variability index (PVI) is described with respect to U.S. Pat. No. 8,414,499, filed Dec. 7, 2007, titled "Plethysmograph Variability Processor" assigned to Masimo and incorporated in its entirety by reference herein. Note that PVI is not to be confused herein with a medical index although PVI may be used to calculate or otherwise indicate one or more medical indices.

As described herein, a medical index 800 is an indicator of the physiological status of a living being. Physiological status may be a positive condition, such as strength, endurance or conditioning, or a negative condition, such as a disease state or physiological weakness, to name a few examples. In an embodiment, a medical index ("index") has a binary value. That is, the index indicates a likelihood of the existence or nonexistence of a particular physiological status such as dehydration 810, renal insufficiency 820, over-hydration 830, gastrointestinal bleeding 840, CHF exacerbation 850 and cardiovascular risk 860, to name a few. In other embodiments, a medical index has a set of discrete values, such as a scale from 1 to 10. For example, 1 may indicate a very low likelihood and 10 a very high likelihood of a particular physiological status. In yet another embodiment, a medical index may have a continuous range of values, such as 0-100% so as to represent, for example, a probability that a particular medical condition exists.

As shown in FIG. 8A, dehydration 810 may be indicated from noninvasive measurements of Hgb, BUN and Cr, and in particular from rising values for each of these constituents over a predetermined time interval "$\Delta t_{dh}$." If available, rising values of PVI over $\Delta t_{dh}$ further indicate dehydration. If available, falling values of BP over $\Delta t_{dh}$ further indicate dehydration.

As shown in FIG. 8B, renal insufficiency 820 may be indicated from noninvasive measurements of Hgb, BUN and Cr, and in particular from falling values of Hgb, relatively fast rising values of BUN and rising to relatively fast rising values of $\Delta t_{ri}$ over a predetermined time interval "$\Delta t_{ri}$." If available, falling values of PVI over $\Delta t_{ri}$ further indicate renal insufficiency. If available, falling values of BP over $\Delta t_{ri}$ further indicate renal insufficiency.

As shown in FIG. 8C, over-hydration 830 may be indicated from noninvasive measurements of Hgb, BUN and Cr, and in particular from falling values of Hgb and BUN over a predetermined time interval "$\Delta t_{oh}$" and relatively constant values of Cr over $\Delta t_{oh}$. If available, falling values of PVI over $\Delta t_{oh}$ further indicate over-hydration. If available, rising values of BP over $\Delta t_{oh}$ further indicate over-hydration.

As shown in FIG. 8D, gastrointestinal bleeding 840 may be indicated from noninvasive measurements of Hgb, BUN and Cr, and in particular from falling levels Hgb over a predetermined time interval "$\Delta t_{gi}$." If available, rising values of PVI over $\Delta t_{gi}$ further indicate gastrointestinal bleeding. If available, falling values of BP over $\Delta t_{gi}$ further indicate gastrointestinal bleeding.

As shown in FIG. 8E, CHF exacerbation 850 may be indicated from noninvasive measurements of Hgb, BUN and Cr, and in particular from stable to falling levels of Hgb and BUN and stable to rising levels of Cr over a predetermined time interval "$\Delta t_{chf}$." If available, falling values of PVI over $\Delta t_{chf}$ further indicate CHF exacerbation. If available, relatively constant or rising values of BP over $\Delta t_{chf}$ further indicate CHF exacerbation.

As shown in FIG. 8F, cardiovascular risk 860 may be indicated from noninvasive measurements of Chol, HDL, Chol/HDL and Trig and in particular from rising levels of Chol, Chol/HDL and Trig and falling levels of HDL over a predetermined time interval "$\Delta t_{cvr}$." If available, rising values of BP over "$\Delta t_{cvr}$." further indicate cardiovascular risk.

In an embodiment $\Delta t_{xx}$ are the same for each index, i.e. $\Delta t_{dh} = \Delta t_{ri} = \Delta t_{oh} = \Delta t_{gi} = \Delta t_{chf} = \Delta t_{cv}$. In an embodiment, $\Delta t_{xx}$ varies for each constituent of a particular index, e.g. $\Delta t_{xx}$(Hgb) $\neq \Delta t_{xx}$ (BUN)$\neq \Delta t_{xx}$(Cr)$\neq \Delta t_{xx}$ (PVI)$\neq \Delta t_{xx}$ (BP). The order of the particular constituents for each index is not intended to indicate the relative weight of that constituent for determining a particular index. For example, the listing of Hgb first in tables 8A-E does not suggest Hgb is more indicative of determining a particular index than BUN, Cr, PVI or BP. In an embodiment, indices are calculated over a fixed $\Delta t$ for one or more constituents. In an embodiment, indices are a function of a delta parameter value over a fixed $\Delta t$, e.g. $\Delta BUN/\Delta t$.

FIG. 9 illustrates trends in various physiological parameters, including blood-constituents, oxygen saturation, blood pressure, respiration rate (RR), temperature and heart-related parameters including heart rate (HR) and electrocardiogram (ECG) waveform features indicative of various physiological conditions, maladies and diseases. The use of one or more of these physiological parameters for determining a particular medical index depends on the availability of sensors, processors and algorithms for measuring these physiological parameters. Further, as noted above, the order of listing of various parameters in this table is not intended to indicate the relative sensitivity of a particular index to these parameters or the relative accuracy of determining a particular index utilizing these parameters.

Medical indices are described with respect to FIGS. 8-9, above, as based upon trends in various physiological parameters, i.e. changes in physiological parameters over time. This advantageously reduces the effect of individual variations in the baseline values for these physiological parameters, especially when the "normal" range for a particular physiological parameter is relatively broad. In other embodiments, however, medical indices may be based upon physiological parameter values in lieu of or in addition to physiological parameter trends, which advantageously allows a spot-check medical index calculation. As such, the up, sideways, and down arrows of FIGS. 8-9 can represent high (or very high), normal, and low (or very low) physiological parameter values so as to indicate a particular index.

In other embodiments, medical indices may be based upon fitness parameters derived, in part, from activity and location sensors, such as accelerometers and GPS devices, so as to measure, as examples, distance walked, calories burned, activity duration and intensity. These measurements may be combined with one or more of the parameters listed in FIG. 9 so as to derive medical indices indicative of exercise tolerance, cardiac function and arrhythmia analysis, to name a few.

A cloud-based physiological monitoring system has been disclosed in detail in connection with various embodiments. These embodiments are disclosed by way of examples only and are not to limit the scope of this disclosure or any claims that follow. One of ordinary skill in art will appreciate many variations and modifications.

What is claimed is:

1. A cloud-based physiological monitoring system comprising:
   one or more sensors in communication with a patient so as to generate one or more data streams responsive to changes in one or more physiological conditions of the patient, wherein the one or more sensors include at least:
      an optical sensor configured to provide a first data stream responsive to at least one of: pulsatile blood flow or a blood constituent parameter, and
      a blood pressure sensor configured to provide a second data stream responsive to blood pressure;
   one or more monitors configured to receive the data streams from the sensors; and a cloud server,
   wherein the one or more monitors are configured to:
      determine whether communication with the cloud server is available or not available;
      responsive to determining that communication with the cloud server is not available, temporarily process the data streams locally; and
      responsive to determining that communication with the cloud server is available, transmit at least indications of the data streams to the cloud server,
   wherein the cloud server is configured to:
      process the data streams, including at least the first and second data streams, so as to derive a plurality of parameters and associated parameter measurements responsive to the changes in the one or more physiological conditions, wherein:
         a first parameter of the plurality of parameters is indicative of hemoglobin (Hgb) of the patient,
         a second parameter of the plurality of parameters is indicative of blood urea nitrogen (BUN) of the patient,
         a third parameter of the plurality of parameters is indicative of creatinine (Cr) of the patient,
         a fourth parameter of the plurality of parameters is indicative of a plethysmograph variability index (PVI) of the patient, and
         a fifth parameter of the plurality of parameters is indicative of a blood pressure of the patient;
      determine that the required parameters for deriving a medical index include the first, second, third, fourth, and fifth parameters, and that the first, second, third, fourth, and fifth parameters are available for deriving the medical index; and
      in response to determining that most-recent parameter measurements associated with the first, second, third, fourth, and fifth parameters satisfy a time frame mismatch tolerance associated with the medical index:
         determine trends in the first, second, third, fourth, and fifth parameters, the trends indicative of changes in the respective first, second, third, fourth, and fifth parameters over time;

derive the medical index based upon a combination of the trends in the first, second, third, fourth, and fifth parameters, the medical index indicating a medical condition of the patient;

communicate the medical index to at least one of the one or more monitors; and cause the at least one monitor to display the medical index.

2. The cloud-based physiological monitoring system according to claim 1, wherein the medical index relates to at least one of: dehydration, renal insufficiency, over hydration, gastrointestinal bleeding, congestive heart failure exacerbation, or cardiovascular risk.

3. The cloud-based physiological monitoring system according to claim 1, wherein the cloud server is further configured to:

in response to determining that the most-recent parameter measurements associated with the first, second, third, fourth, and fifth parameters do not satisfy the time frame mismatch tolerance:

not derive the medical index; and cause the one or more monitors to not display the medical index.

4. The cloud-based physiological monitoring system according to claim 3, wherein causing the one or more monitors to not display the medical index further includes displaying dashes in a location on the monitor where the medical index otherwise would be displayed.

5. A physiological monitoring method comprising:

receiving, from one or more sensors in communication with a patient and via a monitor, sensor data responsive to changes in one or more physiological phenomena of the patient, wherein the one or more sensors include at least an optical sensor and an air-cuff sensor;

determining, by the monitor, whether communication with a cloud server is available or not available;

responsive to determining that communication with the cloud server is not available, temporarily processing the data streams locally at the monitor;

responsive to determining that communication with the cloud server is available, transmitting at least indications of the data streams to the cloud server;

processing, by the cloud server, the sensor data so as to derive a plurality of parameters and associated parameter measurements responsive to the changes in the one or more physiological phenomena, wherein:

a first parameter of the plurality of parameters is indicative of hemoglobin (Hgb) of the patient, a second parameter of the plurality of parameters is indicative of blood urea nitrogen (BUN) of the patient, a third parameter of the plurality of parameters is indicative of creatinine (Cr) of the patient, a fourth parameter of the plurality of parameters is indicative of a plethysmograph variability index (PVI) of the patient, and a fifth parameter of the plurality of parameters is indicative of a blood pressure of the patient;

determining, by the cloud server, that the required parameters for deriving a medical index include the first, second, third, fourth, and fifth parameters, and that the first, second, third, fourth, and fifth parameters are available for deriving the medical index; and in response to determining that most-recent parameter measurements associated with the first, second, third, fourth, and fifth parameters satisfy a time frame mismatch tolerance associated with the medical index:

determining, by the cloud server, trends in the first, second, third, fourth, and fifth parameters, the trends indicative of changes in the respective first, second, third, fourth, and fifth parameters over time;

deriving, by the cloud server, the medical index responsive to a combination of the trends in the first, second, third, fourth, and fifth parameters, the medical index indicating a medical condition of the patient;

communicating, by the cloud server, the medical index to the monitor; and causing display of the medical index on the monitor.

6. The physiological monitoring method according to claim 5 further comprising:

causing display of the medical index on a smart cellular telephone.

7. The physiological monitoring method according to claim 6, wherein the medical index includes an indication of at least one of: dehydration, renal insufficiency, over hydration, gastrointestinal bleeding, congestive heart failure exacerbation, or cardiovascular risk.

8. The physiological monitoring method according to claim 5 further comprising:

in response to determining that the most-recent parameter measurements associated with the first, second, third, fourth, and fifth parameters do not satisfy the time frame mismatch tolerance:

not deriving the medical index; and causing the monitor to not display the medical index.

9. The physiological monitoring method according to claim 5, wherein causing the monitor to not display the medical index further includes causing the monitor to display dashes in a location on the monitor where the medical index otherwise would be displayed.

* * * * *